(12) United States Patent
Miyake et al.

(10) Patent No.: US 6,399,668 B1
(45) Date of Patent: *Jun. 4, 2002

(54) WATER ABSORBENT RESIN

(75) Inventors: Koji Miyake, Himeji; Nobuyuki Harada, Suita; Hiroshi Odanaka, Yokosuka, all of (JP)

(73) Assignee: Nippon Shokubai Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

(21) Appl. No.: 09/112,150

(22) Filed: Jul. 9, 1998

Related U.S. Application Data

(62) Division of application No. 08/453,705, filed on May 30, 1995, now Pat. No. 5,830,543.

(30) Foreign Application Priority Data

May 30, 1994 (JP) .............................................. 6-116947

(51) Int. Cl.$^7$ .................................................. C08J 9/04
(52) U.S. Cl. ......................... 521/92; 521/125; 521/149; 521/91
(58) Field of Search .............................. 428/35.2, 35.5, 428/34.4, 34.5, 35.8, 35.9, 36.5, 913, 76; 206/204, 524.7; 383/37, 200; 521/92, 94, 125, 149, 91

(56) References Cited

U.S. PATENT DOCUMENTS

| | | | |
|---|---|---|---|
| 3,812,856 A | 5/1974 | Duncan et al. ............. 128/285 |
| 4,124,116 A | 11/1978 | McCabe, Jr. ................. 206/204 |
| 4,169,004 A | 9/1979 | Kock et al. .................. 156/227 |
| 4,341,215 A | 7/1982 | Eldridge ...................... 128/285 |
| 4,654,039 A | 3/1987 | Brandt et al. ................ 604/368 |
| 4,725,465 A | 2/1988 | Lastovich .................... 428/35 |
| 4,748,069 A | * 5/1988 | Cullen ........................ 206/204 |
| 4,749,600 A | 6/1988 | Cullen et al. ................. 428/35 |
| 4,839,395 A | 6/1989 | Masamizu et al. ............ 521/56 |
| 5,118,719 A | 6/1992 | Lind ............................ 521/92 |
| 5,147,343 A | 9/1992 | Kellenberger ................ 604/368 |
| 5,149,335 A | 9/1992 | Kellenberger et al. ....... 604/372 |
| 5,154,713 A | 10/1992 | Lind ........................... 604/358 |
| 5,300,358 A | 4/1994 | Evers ........................... 428/286 |
| 5,314,420 A | 5/1994 | Smith et al. ................... 604/358 |
| 5,356,678 A | 10/1994 | Heitzhaus et al. ........... 428/35.6 |
| 5,415,643 A | 5/1995 | Kolb ............................ 604/367 |
| 5,422,405 A | 6/1995 | Dairoku et al. ............... 525/384 |
| 5,424,265 A | 6/1995 | Weinstein .................... 502/400 |
| 5,462,972 A | 10/1995 | Smith et al. ................... 521/53 |
| 5,601,542 A | 2/1997 | Melius et al. ................. 604/368 |
| 5,610,208 A | 3/1997 | Dairoku et al. ............... 525/384 |
| 5,610,220 A | 3/1997 | Klimmek et al. ............. 524/417 |
| 5,712,316 A | 1/1998 | Dahmen et al. ............... 521/72 |
| 5,830,543 A | * 11/1998 | Miyake et al. ............... 428/35.5 |

FOREIGN PATENT DOCUMENTS

| | | |
|---|---|---|
| EP | 0 494 599 A2 | 7/1992 |
| EP | 0 532 002 A1 | 9/1992 |
| JP | 4-235783 A | 8/1992 |
| WO | WO 91/15368 | 10/1991 |

\* cited by examiner

*Primary Examiner*—Rena L. Dye
(74) *Attorney, Agent, or Firm*—Kubovcik & Kubovcik

(57) ABSTRACT

A gelling material is composed of water-absorbent resin 12 wrapped in a bag composed of two laminated water-soluble sheets 1.1, the water-absorbent resin being prepared so as to enable the bag to be disintegrated by an inner pressure generated when an expanded volume of the water-absorbent resin by absorbing water through the bag exceeds a maximum volume capacity. When the gelling material is added to the aqueous fluid, the water-absorbent resin 12 is spread in the aqueous fluid at a stroke, and is diffused uniformly. Thus, the water-absorbent resin 12 is brought fully in contact with the aqueous fluid. Since this enables the aqueous fluid to be gelled in a short period of time, the aqueous fluid can be processed speedily. Even the aqueous fluids, which are difficult to be handled by the conventional gelling material, can be gelled conveniently in a short period of time, and the resulting gel can be easily handled, thereby enabling an easy disposal of the aqueous fluids, i.e., the gel. Additionally, since the water-absorbent resin is spread in the aqueous fluid at a stroke, and is diffused uniformly, a troublesome operation of agitating the aqueous fluid can be eliminated during the gelling process, thereby enabling a simplified gelling process.

17 Claims, 4 Drawing Sheets

WATER ABSORBENT RESIN

This application is a division of application Ser. No. 08/453,705, filed May 30, 1995 now U.S. Pat. No. 5,830,543.

FIELD OF THE INVENTION

The present invention relates to a gelling material for aqueous fluids, such as body fluids like urine, blood, etc., medical wastes like dental wastes, various industrial wastes, water-containing sludge-like wastes, meal wastes having high water content, etc.

BACKGROUND OF THE INVENTION

Known compounds for gelling aqueous fluids, such as body fluids like urine, blood, etc., medical wastes like dental wastes, various industrial wastes, water-containing sludge-like wastes, meal wastes having high water content, etc., include: an inorganic compounds such as bentonite, etc., water-soluble resins such as carboxymethyl cellulose (CMC), polyacrylic acid, etc., water-absorbent resins such as a partially neutralized crosslinked polymer of polyacrylic acid, etc.

To enable easy handling of the above-mentioned inorganic compounds, water-soluble resins, water-absorbent resins, etc., (hereinafter all referred to as water-absorbent resins), various gelling materials have been proposed, wherein water-absorbent resin in the form of powders is wrapped in a bag composed of a water-soluble sheet such as a polyvinyl alcohol film, etc., (hereinafter referred to as a water-absorbent bag), for example, as. disclosed in European Patent No. 494,599.

In order to make the aqueous fluids gel in a short period of time, it is important to bring the water-absorbent resin fully in contact with the aqueous fluid quickly. However, the described conventional gelling materials have the following problems. A long time is required for the water-soluble bag to be dissolved almost completely after the gelling material is added to the aqueous fluid, which causes an unfavorable result that the water-absorbent resin cannot be brought fully in contact with the aqueous fluid until the water-soluble bag is dissolved almost completely. Moreover, it is likely that the dissolved water-soluble bag forms a viscous film so as to surround the water-absorbent resin, which disturbs the expansion of the water-absorbent resin. The described water-absorbent resin has a relatively low water-absorbing rate. Therefore, the described conventional gelling materials have the following problems: Since it takes time for the aqueous fluids to be gelled, the aqueous fluids cannot be processed in a short period of time, and a troublesome operation of agitating the aqueous fluids is required when processing them.

When the gelling material is preserved for a long period of time, the water-absorbent resin absorbs moisture in the air and condenses (so-called caking), etc., which likely to causes a clod to be formed in the water-absorbent resin. For this reason, the water-absorbing capacity of the water-absorbent resin cannot be fully exhibited. The clod formed in the water-absorbent resin makes the gelling process of the aqueous fluids troublesome as the gelling process must be carried out while agitating the aqueous fluids.

SUMMARY OF THE INVENTION

An object of the present invention is to provide a gelling material which permits aqueous fluids to be gelled in a short period of time by dispersing water-absorbent resin in the aqueous fluids quickly and uniformly and adjusting various water-absorbing properties of the water-absorbent resin.

In order to achieve the above object, the gelling material of the aqueous solution in accordance with the present invention is characterized by comprising:

water-absorbent resin wrapped in a bag that is water-soluble at least partially, the water-absorbent resin being prepared so as to enable the bag to be disintegrated by an inner pressure generated when an expanded volume of the water-absorbent resin by absorbing water through said bag exceeds a maximum volume capacity.

According to the described arrangement, since it will not take time for the aqueous fluids to be gelled, the aqueous fluids can be processed speedily. Therefore, even the aqueous fluids which are difficult to be processed by the conventional gelling materials can be gelled conveniently in a short period of time, thereby enabling an easy disposal of the aqueous fluids, i.e., gell. Moreover, the water-absorbent resin is spread in the aqueous fluids at a stroke and is dispersed therein uniformly, the troublesome operation of agitating the aqueous fluids during the gelling process of the aqueous fluids can be eliminated, thereby providing a simplified gelling process.

For a fuller understanding of the nature and advantages of the invention, reference should be made to the ensuing detailed description taken in conjunction with the accompanying drawings.

BRIEF DESCRIPTION OF THE DRAWINGS

FIG. 1 is a schematic sectional view showing a gelling material in accordance with one example of the present invention.

FIG. 2 is a schematic sectional view showing a gelling material in accordance with another example of the present invention.

FIG. 3 is a schematic sectional view showing a gelling material in accordance with still another example of the present invention.

FIG. 4 is a schematic sectional view showing a gelling material in accordance with still another example of the present invention.

FIG. 5 is a schematic sectional view showing a gelling material in accordance with still another example of the present invention.

FIG. 6 is a schematic sectional view showing a gelling material in accordance with still another example of the present invention.

FIG. 7 is a schematic sectional view showing a gelling material in accordance with still another example of the present invention.

FIG. 8 is a schematic sectional view showing a gelling material in accordance with still another example of the present invention.

FIG. 9 is a sectional view showing a schematic configuration of a measuring device for measuring a expansion-diffusing pressure of the water-absorbent resin to be applied to the gelling material.

FIG. 10 is a perspective view showing a schematic configuration of a measuring device for measuring a diffusion index of the water-absorbent resin.

DESCRIPTION OF THE EMBODIMENTS

The following descriptions will explain the present invention in detail.

The water-absorbent resins of the present invention are not particularly limited as long as they are water-insoluble and absorb aqueous fluids quickly. Preferably, the water-absorbent resins of the present invention are obtainable at low price and have excellent water-absorbing properties in terms of safe handling, durability, water-absorbency, water-absorbing rate, water-absorbing power, expansion-diffusing pressure, diffusion index, etc., and are free from the problem of putrefaction.

It is also preferable that the water-absorbent resins of the present invention are prepared so as to have the following properties: the water-absorbing rate of not more than 120 seconds, the expansion-diffusing pressure of not less than 20 kdyn/cm$^2$ and the diffusion index of not less than 50 mm, to achieve the preferable results that the water-absorbent resins can be diffused in the aqueous fluids and absorb them quickly.

The water-absorbing rate suggests a time (seconds) required for 10 ml of 0.9 percent by weight of salt solution (physiological salt solution) maintained at a temperature of 30±0.1° C. placed in a test tube with an inner diameter of 14 mm and a height of 125 mm to be gelled completely after adding thereto 1 g of water-absorbent resin. By setting the water-absorbing rate of the water-absorbent resin to not more than 120 seconds, preferably not more than 60 seconds, the aqueous fluids can be absorbed quickly. The range of the water-absorbing rate above 120 seconds is not preferable because it causes unfavorable results that water-absorbent resin may not absorb the aqueous fluids quickly.

Figure 9:
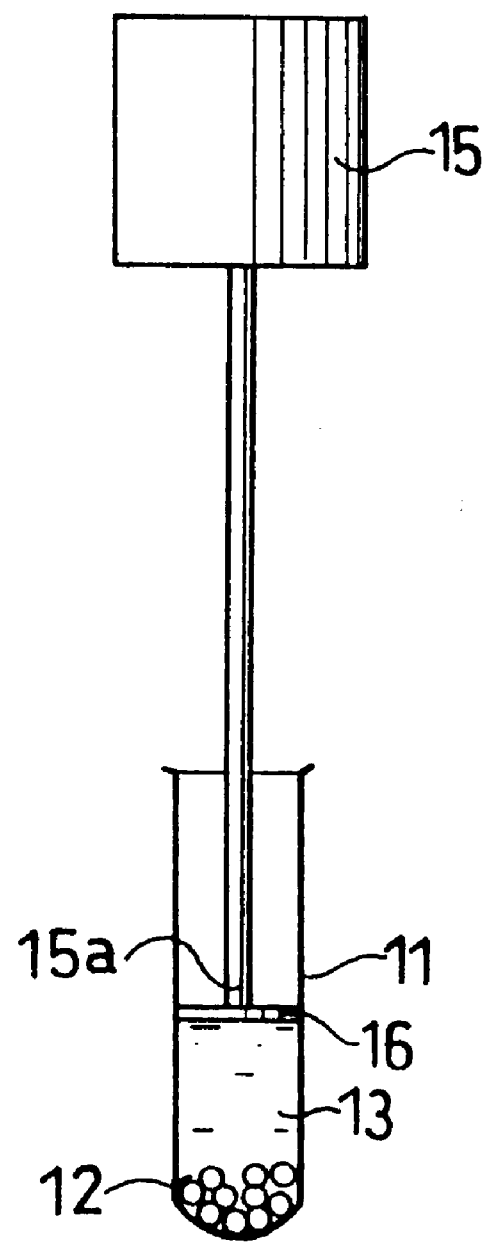

The expansion-diffusing pressure is measured in the following manner. As shown in FIG. 9, in a test tube 11 with an inner diameter of 22 mm and a height of 75 mm, 0.5 g of water-absorbent resin (12) is placed, and the test tube 11 is fixed by, for example, a clamp (not shown), etc. A disc plate 16 having a diameter of 20 mm, a thickness of 1 mm is mounted to a leading end portion 15a (measuring portion) of a digital force gage (pressure gate) 15 (Accuforce Cadet force gage from The Crown Tool and Supply Company, with a measurable range of 0.1 g–500 g).

In the next stage, 10 ml of 0.9 percent by weight of salt solution (13) maintained at a temperature of 30±0.1° C. is placed in the test tube 11. Then, before the water-absorbent resin 12 absorbs the salt solution 13 completely, the leading end portion 15a of the digital force gage 15 is inserted into the text tube 11 so as to put the upper surface of the disk plate 16 upon the surface of the salt solution 13 quickly. Namely, the disk plate 16 is dipped into the salt solution 13.

A force (pressure) of pushing up the disk plate 16 by the water-absorbent resin 12 which expands by absorbing the salt solution 13, i.e., by the cubical expansion of the water-absorbent resin 12, is measured for a period of 30 minutes, and the maximum pressure (g) is calculated. Then, the expansion-diffusing pressure (kdyn/cm$^2$) is computed based on the maximum pressure (g) through the following formula.

Expansion-Diffusing Pressure (kdyn/cm$^2$)=Maximum Pressure (g)× 981/[(1$^2$×π)×1000]

By adjusting the expansion-diffusing pressure of the water-absorbent resin not less than 20 kdyn/cm$^2$, preferably not less than 40 kdyn/cm$^2$, the inner pressure generated when the expanded volume of the water-absorbent resin exceeds the maximum volume of the bag can be made large, which offers the preferable results that the bag can be disintegrated quickly, and it is less likely that the bag thus dissolved disturbs the expansion of the water-absorbent resin. On the other hand, if the expansion-diffusing pressure is less than 20 kdyn/cm$^2$, the inner pressure becomes small, which causes an unfavorable result that the bag is difficult to be disintegrated, and that the water-absorbent resin cannot be diffused in the aqueous fluids quickly. For this reason, the clod is likely to be formed in the water-absorbent resin, and the water-absorbent resin may not absorb the aqueous fluids quickly. Therefore, the above range of the expansion-diffusing pressure is not preferable.

Figure 10:
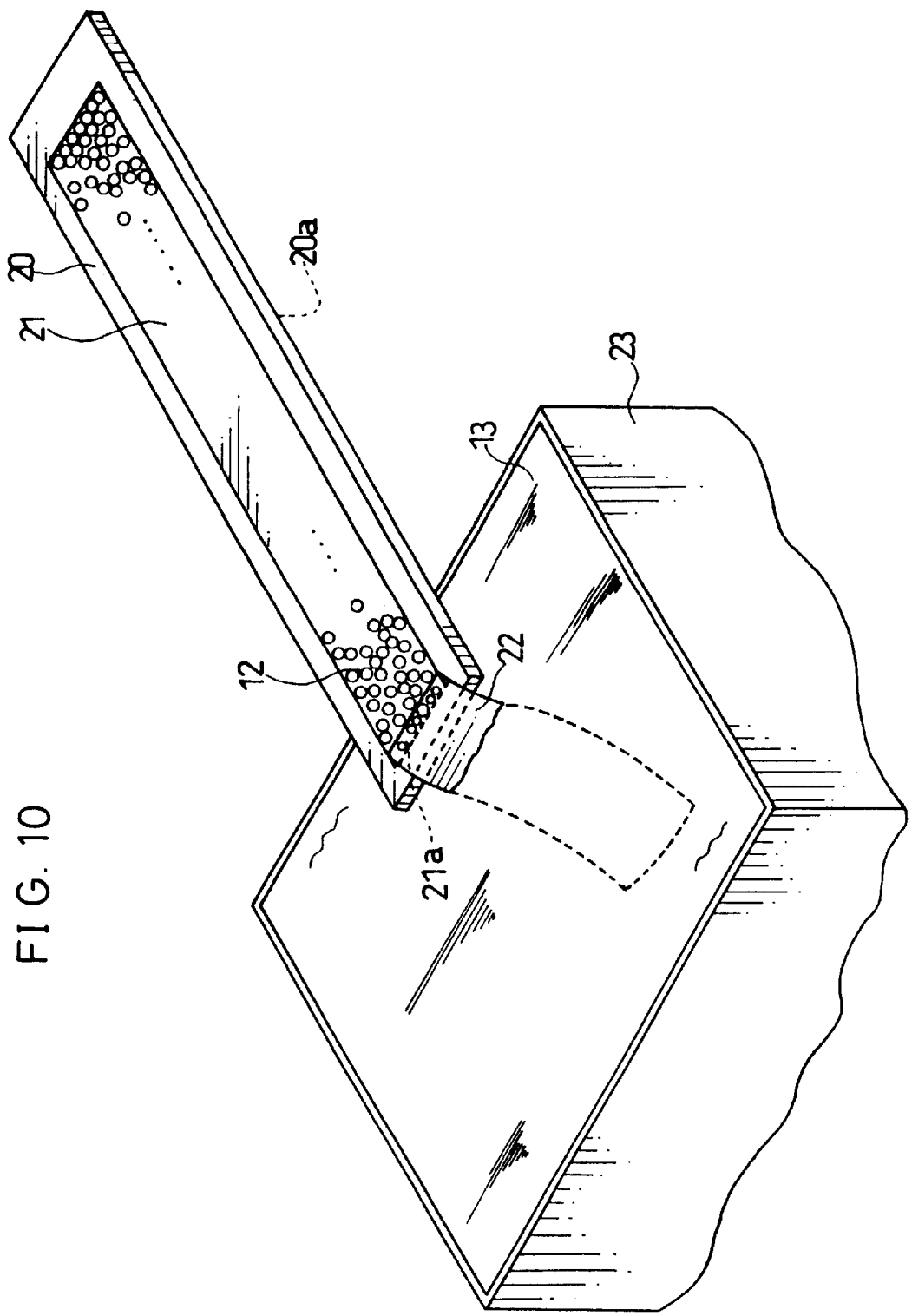

The diffusion index is measured in the following manner. As shown in FIG. 10, an adhesive tape (double coated tape) 21, both surfaces thereof being adhesive, with a width of 30 mm, a length of 150 mm is sealed on a plate 20 with a width of 30 mm, a length of 160 mm and a thickness of 2 mm. Here, one end portion 21a of the adhesive tape 21 is placed in the inside of the edge of the plate 20 by 5 mm. Next, an absorbing paper 22 with a width of 20 mm and a length of 50 mm cut from No. 2 filter paper from The Toyo Filter Paper Co. Ltd. is bonded to the one end portion 21a of the adhesive tape 21. When bonding the absorbing paper 22 to the adhesive tape 21, the width of the flap for fastening is set to 2 mm. Here, the center lines of the plate 20, the adhesive tape 21 and the absorbing paper 22 are overlapped. For the plate 20 and the adhesive tape 21, a water-insoluble (hydrophobic) material is used.

Thereafter, 0.5 g of water-absorbent resin (12) is uniformly dispersed on the adhesive tape 21. As a result, the water-absorbent resin 12 is fixed onto the surface of the adhesive tape 21. On the other hand, the container 23 of a predetermined size is filled with 0.9 percent by weight of the salt solution 13. Then, on the upper end of the container 23, the plate 20 is placed horizontally, and the absorbing sheet 22 is dipped into the salt solution 13. Here, the height of the liquid surface of the salt solution 13 is set substantially equal to the height of the lower surface 20a of the plate 20.

Then, the absorbing paper 22 absorbs the salt solution 13, and it is confirmed with one's eyes that the water-absorbent resin 12 starts expanding by absorbing the salt solution 13. When 10 minutes have passed after the starting of the expansion is confirmed, a length of the area where the salt solution 13 is diffused on the adhesive tape, i.e., from one end portion 21a bonded to the absorbing paper 22 to the boundary between the water-absorbent resin 12 that expanded and the water-absorbent resin 12 did not expand. The length thus measured is referred to as the diffusion index (mm).

By adjusting the diffusion index of the water-absorbent resin not less than 50 mm, more preferably not less than 100 mm, the entire water-absorbent resin wrapped in the bag can absorb the aqueous fluids quickly. If the diffusion index is less than 50 mm, it takes a long time for the aqueous fluids to be diffused (penetrated) in the water-absorbent resin wrapped in the bag, and the clod is likely to generate, thereby presenting the problem that the water-absorbent resin may not absorb the aqueous fluids quickly. For the described reasons, the above range of the diffusion index is not preferable.

Examples of such water-absorbent resins include: a partially neutralized crosslinked polymer of polyacrylic acid; a neutralized graft polymer of starch-acrylic acid, a hydrolyzed graft polymer of starch-acrylonitrile, a saponified copolymer of vinyl acetate-acrylic ester, a crosslinked copolymer of isobutylene-maleic anhydride, a hydrolyzed copolymer of acrylonitrile or copolymer of acrylamide or crosslinked polymers thereof, a cross-linked copolymer of a acrylate-acrylamide, a crosslinked polymer of polyvinyl alcohol, a crosslinked polymer of modified polyethylene oxide, a crosslinked copolymer of acrylamide-2-methylpropanesulfonate, a crosslinked copolymer of (meth) acryloylethane sulfonate, crosslinked carboxymethylate cellulose, a crosslinked polymer of cationic monomer, etc. The above-listed absorbent resins may be used alone or in combination of two kinds or more. Among the above-listed water-absorbent resins, the partially neutralized crosslinked polymer of polyacrylic acid and the neutralized graft polymer of starch-acrylic acid, and a mixture thereof are preferable in terms of water-absorbing properties and safety handling.

Especially, the water-absorbent resins prepared by the following method are preferable for adjusting the water-absorbing properties such as the water-absorbing rate, the expansion-diffusing pressure, the diffusion index, etc., to have preferable values. Namely, a monomer of acrylic acid or acrylate, etc., is used as an aqueous solution, and to the aqueous solution, a foaming agent and, if necessary, a dispersion stabilizer for the foaming agent, etc., is added. Then, the polymerization of the monomer is carried out so as to obtain the water-absorbent resins. Since particle of the water-absorbent resin obtained in the described manner is cellular, the surface area is large, and have excellent water-absorbing properties.

Preferably, the foaming agent is in the form of solid granular with a predetermined particle diameter. Examples of such foaming agents include: magnesium carbonate, calcium carbonate, sodium carbonate having an average particle diameter of 1 $\mu$m–100 $\mu$m. The suitable amount of use of the foaming agent may vary depending on the kinds of the foaming agent and the monomer. Usually around 0.01–5 parts by weight of the foaming agent with respect to 100 parts by weight of the monomer is used. Preferable examples of such dispersion stabilizer include: water-soluble polymer such as hydroxyethyl cellulose, polyethylene oxide, etc., a surface active agent, etc. The suitable amount of use of the dispersion stabilizer may vary depending on the kinds of the dispersion stabilizer, the foaming agent and the monomer, etc. Usually not more than 50 parts by weight of the dispersion stabilizer with respect to the 100 parts by weight of the foaming agent is used. By adding the dispersion stabilizer, the settlement and the agglomeration of the foaming agent in the aqueous solution can be prevented, and the extent of foaming can be controlled.

The above-mentioned water-absorbent resins may be granulated in a predetermined shape, or may be formed into various shapes, such as an irregular fragment-shape, a globular shape, a scaly shape, a bar shape, a bulk-shape, etc. In addition, the water-absorbent resins may be primary particles, or may be granulated bodies of the primary particles. The particle diameter of the water-absorbent resin (for convenience in explanations, hereinafter referred to as a water-absorbent resin particle) is preferably in a range of 0.01–1 mm, more preferably, in a range of 0.1–1 mm considering the kinds of the water-absorbent resin and the use of the gelling material, etc. The method of manufacturing the water-absorbent resin is not limited as long as the water-absorbing properties such as the water-absorbing rate, the expansion-diffusing pressure, the diffusion index, etc., required for the present invention are ensured.

To improve the water-absorbing properties such as the permeability, the diffusivity and the water-absorbing rate, etc., various processes and modifications, etc., are applied to the water-absorbent resin particle. For example, in the case where the water-absorbent resin has a functional group such as a carboxyl group, a sulfonic group, etc., a surface treatment for crosslinking a portion around the surface of the water-absorbent resin particle is applied. This surface treatment can be applied by adding polyhydric alcohol, polyhydric epoxy compound, polyhydric amine compound, a polyvalent metallic salt, etc., which are reactive with the functional group. Examples of such polyhydric alcohol include: glycerine, ethylene glycol, etc. Examples of such polyhydric epoxy compound include: ethylene glycol diglycidyl ether, etc. Examples of such polyhydric amine compound include: ethylenediamine, polyethyleneimine, etc. Examples of polyvalent metallic salt include: aluminum chloride, etc. For example, by projecting an active energy ray such as an electron ray, γ-ray, etc., a portion around the surface of the water-absorbent resin particle can be crosslinked.

Especially, with the combined use of crosslinking agents of at least two kinds having mutually different solubility parameters, as a surface processing agent, the water-absorbent resin having suitable water-absorbing properties for the present invention can be achieved. The suitable amount of the described surface processing agent adopted in the present invention may vary depending on the kinds of the crosslinking agents to be combined, etc. Usually the surface processing agent is used in an amount of 0.001–10 parts by weight, preferably, 0.01–5 parts by weight with respect to 100 parts by weight of solid water-absorbent resin. The above range of the surface processing agent offers the water-absorbent resins which show excellent water-absorbing rate with respect to the physiological salt solution. If the amount of use of the surface processing agent exceeds 10 parts by weight, it is uneconomic because the amount of the surface processing agent in excess of the suitable amount would be wasted. Moreover, it is difficult to adjust the water absorbing properties including water-absorbing rate, etc., to have suitable values.

The water-absorbent resin particle has a crosslinking structure in the inside, and the surface thereof can be cross-linked by the described method. Therefore, the water-absorbing properties of the water-absorbent, resin are controlled. More specifically, the water-absorbent resin particle is arranged so as to have such a crosslinking structure that the surface portion is more dense than the inner portion. As a result, the water-absorbent resin particle is prepared so as to have the water-absorbing rate of not more than 120 seconds, preferably not more than 60 seconds, the expansion-diffusing pressure of not less than 20 kdyn/cm$^2$, preferably not less than 40 kdyn/cm$^2$, and the diffusion index of not less than 50 mm, preferably not less than 100 mm. For the water-absorbent resin of the present invention, it is preferable that the crosslinking density around the surface portion of the particle is higher than that in the inner portion of the particle.

Additionally, by crosslinking the surface portion, the diffusivity of the water-absorbent resin particle can be improved. Therefore, even if the water-absorbent resin is preserved for a long period of time, the agglomeration (a so-called caking), etc., caused by absorbing water would not occur. Therefore, when adding the gelling material to the aqueous fluids, the clod in the water-absorbent resin is not likely to be formed.

Moreover, in order to improve their processability and their quality and performance, for example, the following agents and materials are added to the water-absorbent particles, as occasion demands: fillers made of inorganic fine particles, such as silica fine particles, and pulp fibers or the like; deodorants or deodorizers mainly constituted of zeolite or other materials having activated charcoal, a derivative of iron phthalocyanine, or vegetative essential oil, etc., absorbed thereto; aromatics; anti-fungus agents mainly constituted of metals, such as silver, copper and zinc, and other materials; bactericides; mildewproofing agents; antiseptic agents; deoxidizing agents (antioxidants); surface active agents; foaming agents; and perfumes. Various functions may be imparted to the water-absorbent articles by adding some of these additives thereto. The amounts of these additives to be added may vary depending on the kinds of the additives, etc. Usually the additives are added in an amount of 0.01 percent to 5 percent by weight with respect to the water-absorbent resins. Here, the methods for adding the additives are not particularly limited.

In the case of using the filler, to achieve a still improved water-absorbing rate of the water-absorbent resin, the combined use of the inorganic fine particle and the pulp fiber is preferable. Further, it is also preferable that the silica fine particle is added to the water-absorbent resin because this offer the preferable result that a still improved expansion-diffusing pressure of the water-absorbent resin can be achieved. Namely, the water-absorbent resin having a cellular crosslinked particle surface, having the silica fine particles added thereto is the most preferable.

The water-absorbent resin prepared in the described manner shows high water-absorbing rate, and high expansion-diffusing pressure and diffusion index. For this reason, when adding the gelling material to the aqueous fluids, the water-absorbent resin is dispersed in the aqueous fluids quickly and uniformly. Moreover, the aqueous fluid is diffused (penetrated) into the water-absorbent resin entirely. Namely, the overall water-absorbent resin wrapped in the bag can be gelled in a short period of time. Having the described properties, the water-absorbent resin of the present invention may be used not only as the gelling material but also as a drip-absorbing material and a freshness-retaining material for foods, an absorbent material for sanitary products in the sanitary field like paper diaper, etc., a water-sealing material for cable, water-expandable rubber, a water-retaining material in the gardening and agricultural fields.

The bag, i.e., a sheet which constitutes the bag is not particularly limited. Namely, any sheet which has an appropriate mechanical strength and is permeable into aqueous fluid, i.e., water-permeable sheet (hereinafter referred to as a water-permeable sheet), or any sheet which has an appropriate mechanical strength and is dissolved in the aqueous fluid quickly, i.e., water-soluble sheet (hereinafter referred to as a water-soluble sheet) may be used. Furthermore, the bag which may be made of a sheet having an appropriate mechanical strength and is not permeable to water (hereinafter referred to as a water-impermeable sheet) may be used.

Examples of the material for such water-permeable sheet having fine pores include: paper, non-woven fabric, woven fablic; synthetic film such as polyethylene film, polypropylene film, polyester film, polyamide film, etc. The non-woven fabric is composed of, for example, a synthetic resin fiber such as polyolefin fiber, polyamide fiber, polyester fiber, acrylic fiber, rayon, etc. The woven fabric is composed of, for example, the above-listed synthetic fiber; vegetable fiber such as cotton, hemp, jute, etc.; animal fiber such as wool, etc. Among the above-listed materials, the paper and the non-woven fabric are preferable.

The water-permeable sheet may have permeability to water entirely or partially. Namely, any sheet can be used as long as at least a part of the sheet is water-permeable. For example, the water-permeable sheet may be formed by applying the process for opening fine pores, for example, by projecting a electron beam, etc. The part which is permeable to water may be formed on the water-permeable sheet uniformly or locally.

Examples of the materials for the water-soluble sheet include: a film composed of polyvinyl alcohol (PVA, POVAL), polyethylene oxide (PEO), polypropylene oxide, starch, carrageenan, etc., a sheet produced by papermaking from fabric carboxymethyl cellulose and cellulose fiber, etc. This paper sheet is dissolved when it is brought in contact with the aqueous fluid (water-degradability). Among the above-listed materials, polyvinyl alcohol is preferable. The water-soluble sheet includes a water-permeable sheet and a water-impermeable sheet partially made of a water-soluble material.

The examples of the materials for the water-impermeable sheet include: synthetic resin film such as a low density polyethylene film, a polypropylene film, a polyester film, a polyamide film, etc.

Figure 1:
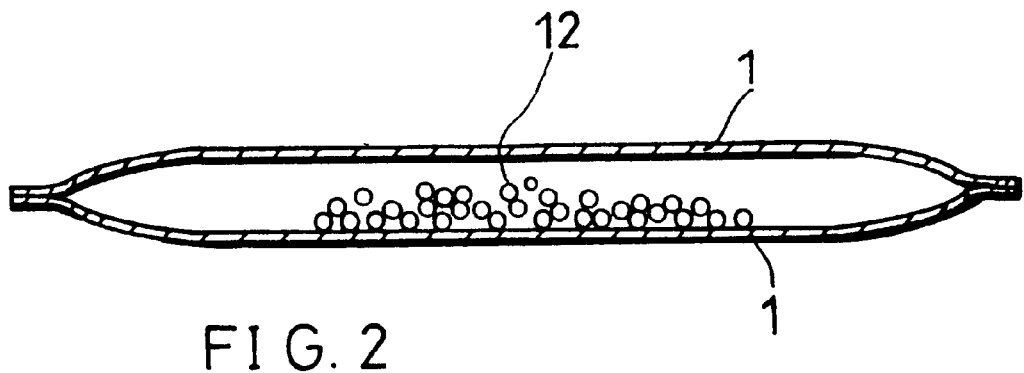
FIGS. 1 through FIG. 10 show one embodiment of the present invention.
Figure 2:
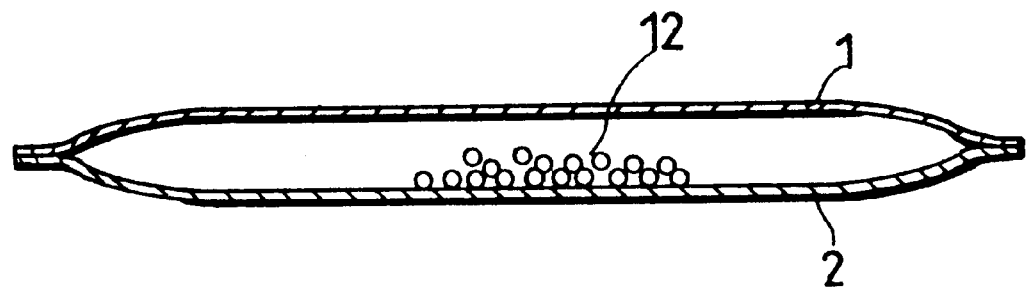
Figure 3:
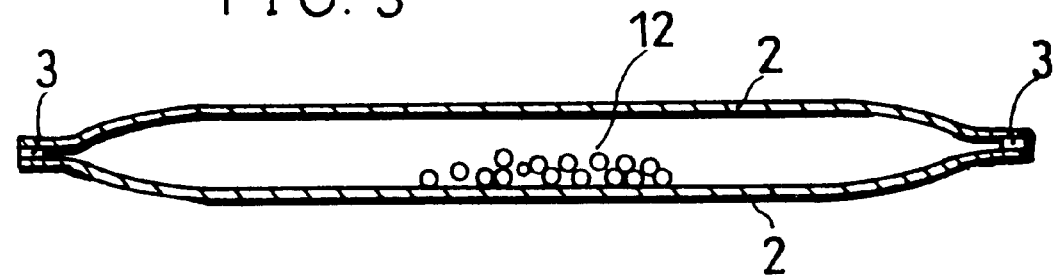
Figure 4:
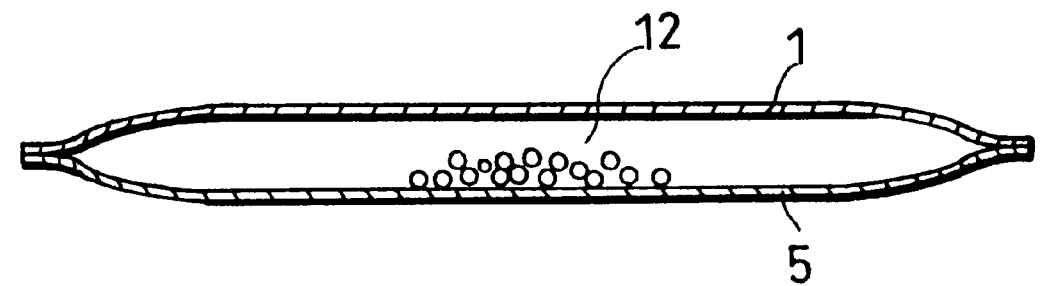
Figure 5:
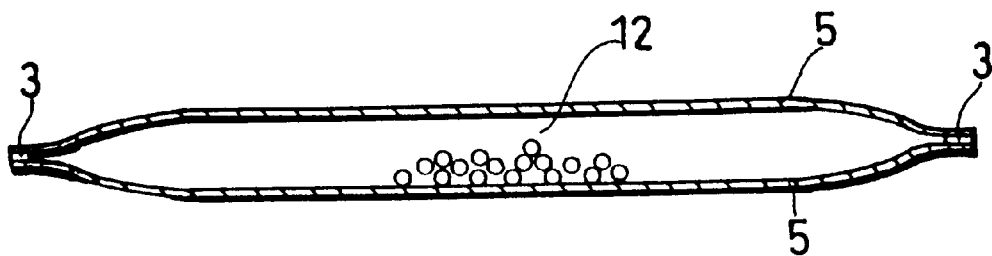

The bag to be adopted in the present embodiment may be produced by laminating two water-soluble sheets 1.1 as shown in FIG. 1, or by laminating the water-soluble sheet 1 and the water-permeable sheet 2 as shown in FIG. 2. Alternatively, the bag of the present embodiment may be produced by laminating two water-permeable sheets 2 using the adhesive 3 as shown in FIG. 3. Namely, the sheets of the bag may be any combination of the water-sbluble sheets 1.1, the water soluble sheet 1 and the water-permeable sheet 2, and the water permeable sheets 2.2. Further, the bag in the present embodiment may be produced by laminating the water-soluble sheet 1 and the water-permeable sheet 5 as shown in FIG. 4. Or the bag in the present embodiment may be produced by laminating two water-impermeable sheets 5.5 by the adhesive 3 as shown in FIG. 5. Namely, the bag in the present embodiment is not limited as long as at least a part of the sheet or the adhesive has water-solubility. As shown in FIG. 1 through FIG. 5, the gelling material is composed of the water-absorbent resin 12 wrapped in the bag. Here, the bag may be composed of a folded sheet.

The size, the shape, etc., of the sheet are not particularly limited. As to the thickness of the sheet, the thinner sheet is preferable as long as a desired mechanical strength can be ensured. By wrapping the water-absorbent resin into the bag, an easy handling of the water-absorbent resin can be achieved.

For example, when the bag is produced by laminating two water-soluble sheets, the water-insoluble sheet and the water-permeable sheet, or the water-soluble sheet and the water-impermeable sheet, namely, in the case of laminating two sheets without using the water-soluble adhesive, the method of laminating these sheets is not particularly limited. For example, the respective fringe portions of the two sheets may be laminated using an appropriate adhesive. Alternatively, the two sheets may be laminated by heat-sealing along edges of the two sheets. Furthermore, the two sheets may be laminated by applying thereto an ultrasonic welding. Among the above-listed laminating methods, the heat-sealing method or the method using the adhesive are preferable. In the case of adopting these methods, the water-insoluble agent may be used as well.

The water-soluble adhesive for use in laminating these sheets is not particularly limited as long as the sheets can be laminated firmly. Examples of such additive include: rubber dispersion, starch paste, vinyl acetate adhesive, polyvinyl alcohol, polyethylene oxide, etc. By applying an appropriate amount of adhesive to the edges of the sheets, the sheets can be bonded firmly. Theses adhesives are quickly dissolved when the gelling material is added to the aqueous fluids. As a result, the sheets are pealed from one another, i.e., these two sheets are separated completely, and the bag is opened.

In order to prepare the bag to be easily disintegrated by an inner pressure generated as the water-absorbent resin expands, for example, the portion having a weaker mechanical strength than the other portions may be formed, for example, by forming scores, i.e., multiple stitches in a line. Namely, the portion which can be easily disintegrated by the inner pressure may be formed. The method of producing such bag is not particularly limited.

In the gelling material of the present invention, suitable amount of the water-absorbent resin may vary depending on the combination of the various factors such as the quality, thickness, size, mechanical strength, etc., of the material of the bag, and the water-absorbing properties of the water-absorbent resin, or the amount and the use of the aqueous fluids, etc. Namely, the appropriate amount of water-absorbent resin should be set considering the above-mentioned factors so that the bag can be disintegrated by an inner pressure, generated when the expanded volume by absorbing water through the bag, exceeds the maximum volume capacity of the bag according to conditions. However, if the aqueous fluid to be gelled includes an organic substance such as oil, protein, etc., or salt, etc., the water-absorbing properties would be slightly lowered. Therefore, a slightly greater amount the water-absorbent resin should be added. In general, the water-absorbent resin can absorb water in the amount of tens to hundreds times of its dead weight. Namely, the magnification of the water-absorbency of the water-absorbent resin is in a range between several tens times to several hundreds times.

The water-soluble sheet has such a drawback that it takes a long time to be dissolved completely after being placed in the aqueous fluids. However, in the case of adopting the bag produced by laminating the water-permeable sheet and the water-soluble sheet, before the water-soluble resin is dissolved almost completely, the aqueous fluid penetrates into the inside of the bag through the water-permeable sheet. Then, the water-absorbent resin expands by absorbing the aqueous fluid thus penetrated. As a result, the bag is disintegrated by the inner pressure. For this reason, before the water-soluble sheet is dissolved almost completely, the water-absorbent resin is spread at a stroke and is diffused in the aqueous fluid uniformly.

In the case of adopting the bag composed of two water-permeable sheets using a water-soluble adhesive, before the adhesive is dissolved in the aqueous fluid almost completely, the aqueous fluid penetrates into the inside of the bag through the water-permeable sheets. Then, the water-absorbent resin expands by absorbing the aqueous fluids thus penetrated. As a result, the bag is disintegrated, namely, the two sheets are separated by the inner pressure. While the adhesive being dissolved, the water-absorbent resin is spread in the aqueous fluid at a stroke and is diffused uniformly.

When the gelling material is added to the aqueous fluid, the bag is disintegrated quickly, and the water-absorbent resin can be made in fully in contact with the aqueous fluid quickly. Additionally, the water-absorbent resin is prepared so as to have the following water absorbing-properties: water-absorbing rate of not more than 120 seconds, the expansion-diffusing pressure of not less than 20 kdyn/cm$^2$ and the diffusion index of not less than 50 mm. The water-absorbent resin having the described properties can be diffused in and absorb the aqueous solution without forming a clod. Since the gelling material in accordance with the present invention enables the aqueous fluid to be gelled in a short period of time, the aqueous fluids can be processed quickly. This enables even the water-absorbent resins which are difficult to be handed by the conventional gelling material can be converted into a gell conveniently in a short period of time, and the resulting gell to be handled easily, thereby enabling an easy disposal of the aqueous fluids, i.e., the gell. Additionally, since the water-absorbent resin is spread in the aqueous fluid at a stroke and is diffused uniformly, a troublesome operation of agitating the aqueous fluid during the gelling process can be eliminated, thereby enabling a simplified gelling process.

Figure 6:
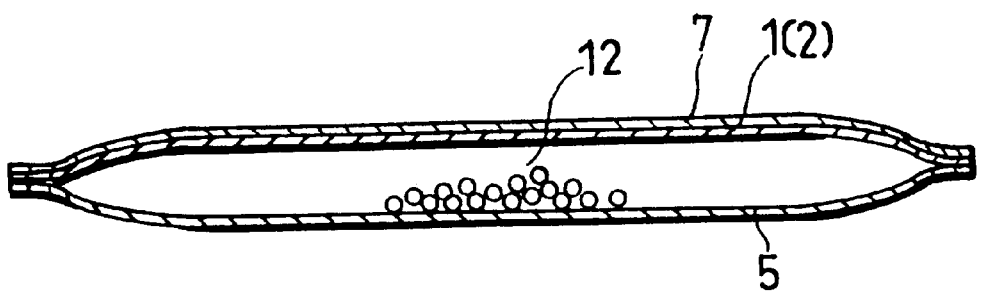
Figure 7:
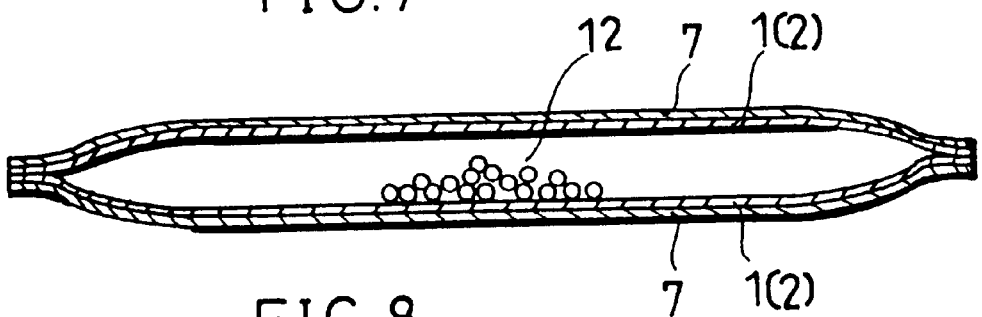
Figure 8:
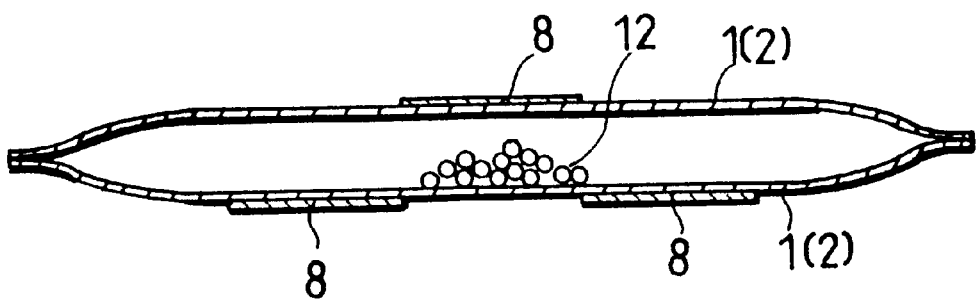

In the present invention, the outer bag for wrapping therein the gelling material (hereinafter referred to as the gelling material main body for convenience in explanations) is not limited as long as it has an appropriate mechanical strength, and is composed of a water-impermeable material. The outer bags of the present invention include not only the bags made of a synthetic resin film, etc., but also containers, like cans, bottles, etc., made of metal, glass, synthetic resin, etc., and also include an outer bag composed of water-impermeable sheets 7 laminated on the outer surface of a water-soluble sheet 1 (or a water-permeable sheet 2) in a separable manner so as to cover the water-soluble sheet 1 (or water-permeable sheet 2) as shown in FIG. 6 and FIG. 7, an outer bag composed of water-impermeable seals 8 laminated only on portions of the outer surface having water-solubility or water-permeability shown in FIG. 8. Among the above-listed bags, the bag made of the synthetic resin film, etc., the water-impermeable sheet, the water-impermeable seal are preferable, considering conveniences in transportation, storage, handling, etc. Examples of such synthetic resin film include: low density polyethylene film, polypropylene film, polyester film, polyamide film, etc. In the case of adopting the outer bag composed of the water-impermeable sheets or water-impermeable seals, the water-impermeable portions of the gelling material main body serve as the outer bag.

To make the handling of the gelling material main body easier during the process, for example, scores, i.e., multiple stitches may be formed in a line at a predetermined position, or a so-called zipper may be formed. In some cases, the opening portion of the bag is closed using a rubber band, a lace, etc. Namely, the bag which enables the gelling material main body to be wrapped therein and the gelling material main body to be quickly taken out is preferable. In the case where the bag is made of the water-impermeable sheet or the water-impermeable seal, the bag which can be quickly separated from the gelling material main body while being used is preferable. The method of producing the gelling material main body is not particularly limited. Similarly, the method of laminating the water-impermeable sheet and the water-impermeable seal onto the bag is not particularly limited.

By wrapping the gelling material main body in the bag, the gelling material main body, i.e., the water-absorbent resin can be prevented from absorbing moisture in the air while being stored. Therefore, the gelling material main body can be preserved in stable conditions for a long period of time. Additionally, the gelling material main body can be preserved even under humid conditions. If the gelling material main body is preserved for a long period of time without being wrapped in the bag, the water-absorbent resin may condense by absorbing moisture in the air. Therefore, when adding the gelling material main body to the aqueous fluid, the clod is likely to be formed in the water-absorbent resin, which would result in a lowered water-absorbing capacity of the water-absorbent resin. Thus, the gelling material main body that is not wrapped in the bag is not preferable.

In the case of adopting the above-mentioned gelling material, the gelling material main body is taken out of the outer bag, and is placed in the aqueous fluid filled in a container like a bucket, etc. Alternatively, the container may be filled with the gelling material main body beforehand, and the aqueous fluid is put in the container. Since the water-absorbent resin is wrapped in the bag, the gelling material can be added to the aqueous fluid conveniently. Examples of such aqueous fluids include: body fluids, such as urine, blood, etc., medical wastes such as dental wastes, various industrial wastes, water-containing sludge-like wastes, meal wastes having high water content, etc. However, the aqueous fluids of the present invention are not limited to the above. In the case of gelling the aqueous fluid in which a large amount of solid substance is mixed, such as meal wastes having high water content, the aqueous fluid may be agitated during the gelling process if necessary.

As described, the gelling material of the present invention is composed of the water-absorbent resin wrapped in a bag that is water-soluble at least partially, the water-absorbent resin being prepared so as to enable the bag to be disintegrated by an inner pressure generated when an expanded volume of the water-absorbent resin by absorbing water through said bag exceeds a maximum volume capacity. The bag is composed of a sheet that is water-permeable at least partially and a water-soluble sheet which are laminated. The bag may be produced by laminating these sheets using a water-soluble adhesive. The water-absorbent resin has the following water-absorbing properties: the water-absorbing rate of not more than 120 seconds, the expansion-diffusing pressure of not less than 20 kdyn/cm$^2$, and the diffusion index of not less than 50 mm.

Therefore, when the gelling material is added to the aqueous fluid, since the bag can be disintegrated quickly, the water-absorbent resin can be made fully in contact with the aqueous fluid quickly without being prevented from expanding by the bag thus dissolved. Moreover, the water-absorbent resin can be dissolved in and absorb the aqueous solution quickly without forming a clod. Therefore, the gelling material in accordance with the present invention enables the aqueous fluid to be gelled in a short period of time, and the aqueous fluids can be processed quickly. Therefore, even the aqueous fluids, which are difficult to be handled by the conventional gelling material, can be converted into a gell conveniently in a short period of time, and the resulting gell can be handled easily, thereby enabling an easy disposal of the aqueous fluids, i.e., the gell. Moreover, since the water-absorbent resin is spread in the aqueous fluid at a stroke and is diffused uniformly, a troublesome operation of agitating the aqueous fluid during the gelling process can be eliminated, thereby enabling a simplified gelling process.

The gelling material of the present invention is arranged such that the bag is wrapped in the water-impermeable outer bag. Since this outer bag prevents the gelling material main body, i.e., the water-absorbent resin from absorbing moisture in the air while being preserved, the water-absorbency of the water-absorbent resin can be fully exhibited when it is actually used. Therefore, the gelling material main body can be preserved for a long period of time in stable conditions even under humid conditions.

The gelling material of the present invention can be applied to various fields which require the aqueous fluids to be processed. Especially, the gelling material is effective when processing meal wastes resulting from, for example, meals in the airplane, etc., coffee wastes, etc. Additionally, by selecting a suitable material for the bag and adjusting the amount of the water-absorbent resin to be added, the gelling material of the present invention may be suitably used as drip-absorbing materials, freshness-retaining materials for meat, fish, etc., sanitary products in the sanitary field like paper diaper, etc. Suitable size and shape of the gelling material are not particularly limited, but are set according to the use, cost, etc., of the gelling material.

The following examples and comparative examples are presented for the purpose of illustration only, and are not to be construed as limiting the scope of the invention in any way. The properties of the resulting absorbent resins were measured in manners presented below.

[Water-absorbent Resin Preparation Method 1]

In 414 g of acrylic acid, 4380 g of 37 percent by weight of sodium acrylic acid and 670 g of deionized water were added, and thereafter, 6.8 g of trimethylolpropane triacrylate (crosslinking agent) was dissolved therein to give a reaction solution. In a stainless steel reactor of two-arms type kneader with a cover equipped with a jacket (volume content: 10 L) with two sigma blades, the reaction solution was placed, and the reaction system was displaced by introducing nitrogen gas while removing oxygen from the solution. While agitating the reaction solution maintained at 35° C. by circulating hot water in the jacket, 2.6 g of ammonium persulfate (polymerization initiator) and 0.12 g of sodium hydrogen sulfate were added to initiate the polymerization.

A water-containing gell-like polymer obtained at a peak of the polymerization was a finely divided polymer with a diameter of around 5 mm. After leaving it for 60 minutes, the reaction was stopped and the resulting finely divided water-containing gel-like polymer was taken out.

After the resulting water-containing gel-like polymer was dried for two hours at 150° C., the resulting dried polymer was pulverized by a vibrating mill, etc., and further classified by a wire netting of 20 mesh. As a result, a comparative water-absorbent resin without having a surface treatment (hereinafter simply referred to as a comparative water-absorbent resin) was obtained. The comparative water-absorbent resin has the water-absorbing rate of 2 minutes and 30 seconds, the expansion-diffusing pressure of 2.8 kdyn/cm$^2$ and the diffusion index of 15 mm.

Thereafter, to 100 parts by weight (hereinafter referred to as parts) of the comparative water-absorbent resin, added and mixed were 0.05 parts of diethylene glycol diglycidyl ether, 0.5 parts of glycerine, 3 parts of water and 0.75 parts of isopropyl alcohol. The resulting mixture was heated for 35 minutes at 200° C.

As a result, water-absorbent resin A with a surface treatment was obtained. The magnification of the water-absorbency of water-absorbent resin A was 300 times with respect to pure water and 40 times with respect to 0.9 percent by weight of salt solution (physiologic salt solution). The water-absorbing rate, the expansion-diffusing pressure and the diffusion index of the water-absorbent resin A were respectively 50 seconds, 25.4 kdyn/cm$^2$ and 54 mm.

Further, to 100 parts of water-absorbent resin A, added and mixed was 0.5 parts of silica fine particles (AEROSIL 200 from NIPPON AEROSIL CO., LTD) as a filler. As a result, water-absorbent resin B was obtained. The magnification of the water-absorbency of the water-absorbent resin was 300 times with respect to pure water and 40 times with respect to 0.9 percent by weight of salt solution (physiologic salt solution). The water-absorbing rate, the expansion-diffusing pressure and the diffusion index of the water-absorbent resin were respectively 25 seconds, 59.8 kdyn/cm$^2$ and the diffusion index of 112 mm.

[Water-absorbent Resin Preparation Method 2]

To 43 parts of acrylic acid, 355 parts of 37 percent by weight of sodium acrylic acid and 54 parts of deionized water were added, and thereafter, 0.8 parts of polyethylene glycol diacrylate (crosslinking agent), 1 part of hydroxyethyl cellulose (dispersion stabilizer) and 0.1 parts of sorbitan monostearate (surface active agent) were dissolved therein to give a reaction solution. In the reactor used in the Preparation Method 1, the reaction solution was placed, and the reaction system was displaced by introducing nitrogen gas while removing oxygen from the solution. While agitating the reaction solution maintained at 20° C., dispersed was 4 parts of magnesium carbonate (foaming agent) with an average particle diameter of around 5 μm) and further added were 0.25 parts of sodium persulfate and 0.001 parts of L-ascorbic acid.

Thereafter, the reaction solution was put into a vat (flat plate) up to a depth of 5 mm, and the polymerization was performed in the vat. After leaving it for around 10 minutes, the temperature of the reaction solution reaches around 80° C. Thereafter, the polymerization was further carried out while maintaining the reaction solution at 70–80° C. As a result, a cellular water-containing gel-like polymer in plate shape with a thickness of around 5 mm was obtained.

After the resulting water-containing gel-like polymer was dried for two hours at 150° C., the resulting dried polymer was pulverized by a vibrating mill, etc., and further classified by a wire netting of 20 mesh. As a result, water-absorbent resin in granular form was obtained.

To 100 parts of the resulting water-absorbent resin, added and mixed were 0.05 parts of ethylene glycol diglycidyl ether, 0.5 parts of glycerine, 3 parts of water and 0.75 parts of isopropyl alcohol. The resulting mixture was heated for 60 minutes at 210 ° C.

As a result, cellular water-absorbent resin with a surface treatment was obtained. To 100 parts of the resulting water-absorbent resin, further added and mixed were added 0.4 parts of silica fine particles (AEROSIL 200V from NIPPON AEROSIL CO., LTD) as a filler. As a result, water-absorbent resin C was obtained. The magnification of the water absorbency of the water-absorbent resin was 320 times with respect to pure water and 45 times with respect to 0.9 percent by weight of salt solution (physiologic salt solution). The water-absorbing rate, expansion-diffusing pressure and the diffusion index of the water-absorbent resin were respectively 16 seconds, 82.7 kdyn/cm$^2$ and the diffusion index of 130 mm.

With respect to three kinds of commercially available water-absorbent reins (Sanyo Chemical Industries, Ltd., SANWET IM-100, SANWET IM-2200 and SANWET IM-5000), the respective water-absorbancies, the expansion-diffusing pressures and the diffusion indexes were measured. These water-absorbent resins are hereinafter referred to as commercially available water-absorbent resins A, B and C in the above listed order of the products. The respective water-absorbing rates of the commercially available water-absorbent resins A, B and C are 7 minutes 10 seconds, 30 seconds, and 5 minutes 20 seconds. The respective expansion-diffusing pressures of the commercially available water-absorbent resins A, B and C are 2.7 kdyn/cm$^2$, 9.5 kdyn/cm$^2$ and 16.8 kdyn/cm$^2$. The respective diffusion indexes of the commercially advisable water-absorbent resins A, B and C are 15 mm, 17 mm and 52 mm.

EXAMPLE 1

A bag was produced by heat sealing along three edges of two overlapped water-soluble polyvinyl alcohol (poval) films cut into 10 cm×10 cm in size. Then, 100 g of absorbent resin B was put in the bag, and its opening was heat sealed, thereby obtaining a gelling material main body. The resulting gelling material main body was wrapped in an outer bag with a zipper, made of polyethylene, thereby obtaining a gelling material.

The resulting gelling material was preserved in a room for a long period of time, and the agglomeration (a so-called caking) of the water-absorbent resin particles was not generated. Then, the gelling material main body was taken out of the outer bag, and was immediately put into the container made of polyethylene with an inner volume of 3 L, that was filled with 2 L of blood waste (aqueous fluids). The bag was dissolved and disintegrated quickly, and the water-absorbent resin B was diffused in the blood waste quickly. The overall blood waste was gelled in around 20 seconds without generating a clod in the water-absorbent resin B.

EXAMPLE 2

A bag was produced by heat sealing along three edges of two overlapped pieces of 10 cm×10 cm in size cut from a water-soluble polyvinyl alcohol (poval) film (water-soluble sheet) and from so-called paper towel (water-permeable sheet). Then, 70 g of water-absorbent resin A was put in the bag, and then its opening was heat sealed, thereby obtaining a gelling material main body. The resulting gelling material main body was wrapped in an outer bag with a zipper made of polyethylene, thereby obtaining a gelling material.

The resulting gelling material was preserved in a room for a long period of time, and the agglomeration (a so-called caking) of the water-absorbent resin A was not generated. Then, the gelling material main body was taken out of the outer bag, and was immediately put into a bucket made of synthetic resin with an inner volume of 10 L filled with 5 L of coffee waste (aqueous fluid). The bag was dissolved and disintegrated quickly, and the water-absorbent resin A was diffused in the coffee waste quickly. The overall coffee waste was gelled in around 30 seconds without generating a clod in the water-absorbent resin A.

EXAMPLE 3

A bag was produced by sealing with rubber dispersion (adhesive) along three edges of two overlapped pieces 10 cm×10 cm in size cut from so-called paper towel (water-permeable sheet). Then, 70 g of water-absorbent resin B was put in the bag, and then its opening was heat sealed, thereby obtaining a gelling material main body. The resulting gelling material main body was wrapped in an outer bag with a zipper made of polyethylene having formed thereon multiple stitches in a line, thereby obtaining a gelling material.

The gelling material was preserved in a room for a long period of time, and the agglomeration (a so-called caking) of the water-absorbent resin B was not generated. Then, the gelling material main body was taken out of the outer bag, and was immediately put into a bucket made of synthetic resin with an inner volume of 10 L filled with 5 L of meal waste (aqueous fluid). The two laminated sheets of the bag were separated quickly, and the water-absorbent resin B was diffused in the meal waste quickly. The overall meal waste was gelled completely in around 20 seconds without generating a clod of the water-absorbent resin B.

EXAMPLE 4

A bag was produced by heat sealing along two edges of a folded piece (12 cm×10 cm) of 24 cm×10 cm in size of a polyvinyl alcohol (poval) film (water-soluble sheet). The, 100 g of water-absorbent resin C was put into the bag, and then its opening was heat sealed, thereby obtaining a gelling material main body. The resulting gelling material main body was wrapped in an outer bag with a zipper made of polyethylene, thereby obtaining a gelling material.

The resulting gelling material was preserved for a long period of time, and the agglomeration of the water-absorbent resin C was not generated. Then, the gelling material main body was taken out of the outer bag, and was immediately put into a container made of polyethylene with an inner volume of 3 L filled with 2 L of blood waste (aqueous fluid). The bag was dissolved and disintegrated quickly, and the water-absorbent resin C was diffused in the blood waste quickly. The overall blood waste was gelled in around 15 seconds without forming a clod of the water-absorbent resin C.

Comparative Example 1

The same preparation procedure as in Example 1 was conducted except that 100 g of a commercially available water-absorbent resin A was used in replace of 100 g of water-absorbent resin B of Example 1, and a comparative gelling material was obtained. After leaving it for a long period of time, the gelling material main body was taken out of the outer bag, and was immediately put into the container made of polyethylene with an inner volume of 3 L filled with 2 L of blood waste (aqueous fluid). The bag was not disintegrated quickly, which caused the unfavorable results that the comparative water-absorbent resin was not diffused in the blood waste uniformly and a clod was formed in the water-absorbent resin. In order to eliminate the clod, the blood waste was agitated with a stick during the gelling process, and still it took around 5 minutes for the overall blood waste to be gelled.

Comparative Example 2

The same preparation procedure as in Example 1 was conducted except that 100 g of comparative water-absorbent resin was used in replace of 100 g of water-absorbent resin B of Example 1, and a comparative gelling material was obtained. After leaving it for a long period of time, the gelling material main body was taken out of the outer bag, and was immediately put into the container made of polyethylene with an inner volume of 3 L filled with 2 L of blood waste (aqueous fluid). The bag was not disintegrated quickly, which caused unfavorable results that the comparative water-absorbent resin was not diffused in the blood waste uniformly and a clod was formed in the water-absorbent resin. In order to eliminate the clod, the blood waste was agitated during the gelling process with a stick, and still it took around 120 seconds for the overall blood waste to be gelled.

Comparative Example 3

The gelling material main body of Example 1 was preserved in a room for a long period of time without being wrapped in the outer bag. As a result, the agglomeration was formed in a part of the water-absorbent resin B. Then, the gelling material main body was taken out of the outer bag, and was immediately put into the container made of polyethylene with an inner volume of 3 L filled with 2 L of blood waste (aqueous fluid). The bag was not disintegrated quickly which caused unfavorable results that the comparative water-absorbent resin was not diffused in the blood waste uniformly and a clod was formed in the water-absorbent resin B. In order to eliminate the clod, the blood waste was agitated with a stick during the gelling process, and still it took around 120 seconds for the overall blood waste to be gelled.

Comparative Example 4

The same preparation procedure as in Example 1 was conducted except that 100 g of commercially available water-absorbent resin B was used in replace of 100 g of water-absorbent resin B of Example 1, and a comparative gelling material was obtained. After leaving it for a long period of time, the gelling material main body was taken out of the outer bag, and was immediately put into the container made of polyethylene with an inner volume of 3 L filled with 2 L of blood waste (aqueous fluid). The bag was not disintegrated quickly and a part of the water-soluble poval film of the bag adhered to the surface of the commercially available water-absorbent resin B. Thus, the commercially available water-absorbent resin was not diffused in the blood waste uniformly and a clod was formed in the water-absorbent resin B. In order to eliminate the clod, the blood waste was agitated with a stick during the gelling process, and still it took around 4 minutes for the overall blood waste to be gelled.

Comparative Example 5

The same preparation procedure as in Example 1 was conducted except that 100 g of a commercially available water-absorbent resin C was used in replace of 100 g of water-absorbent resin B of Example 1, and a comparative gelling material was obtained. After leaving it for a long period of time, the gelling material main body was taken out of the outer bag, and was immediately put into the container made of polyethylene with an inner volume of 3 L filled with 2 L of blood waste (aqueous fluids). The bag was not disintegrated quickly, and a part of the water-soluble poval film of the bag adhered to the surface of the commercially available resin C. Thus, the comparative water-absorbent resin was not dispersed in the blood waste uniformly and a clod of the water-absorbent resin was formed. In order to eliminate the clod, the blood waste was agitated with a stick during the gelling process, and still it took around 5 minutes for the overall blood waste to be gelled.

As is clear from Examples 1–4 and Comparative Examples 1–5, the gelling materials of the present embodiment enabled the aqueous fluids to be gelled in a shorter period of time compared with the comparative gelling materials. Moreover, since the water-absorbent resin was spread in the aqueous fluid at a stroke, and was diffused uniformly, the troublesome operation of agitating the aqueous fluids during the gelling process was not required, thereby permitting a simple gelling method for the aqueous fluids. Furthermore, the gelling materials of the present invention can be preserved in stable conditions for a long period.

The invention being thus described, it will be obvious that the same way be varied in many ways. Such variations are not to be regarded as a departure from the spirit and scope of the invention, and all such modifications as would be obvious to one skilled in the art are intended to be included within the scope of the following claims.

What is claimed is:

1. A water-absorbent resin comprising a water-absorbent resin particle having a crosslinking structure in an inside of the particle, the particle having a surface which has been subjected to a cross-linking treatment for cross-linking the surface, the water-absorbent resin having the following water-absorbing properties: water-absorbing rate of not more than 120 seconds, expansion-diffusing pressure of not less than 20 kdyn/cm$^2$ and diffusion index of not less than 50 mm.

2. The water-absorbent resin as set forth in claim 1, wherein said water-absorbent resin particle is prepared by polymerizing acrylic acid or salts thereof in water in a presence of a foaming agent in a solid granular form having an average diameter of 1–100 μm.

3. The water-absorbent resin as set forth in claim 2, wherein:

said foaming agent is a material of at least one kind selected from the group consisting of magnesium carbonate, calcium carbonate and sodium carbonate.

4. The water-absorbent resin as set forth in claim 1, wherein said water-absorbent resin particle is prepared by polymerizing acrylic acid or salts thereof in water in a presence of a foaming agent in a solid granular form having an average diameter of 1–100 μm and a dispersion stabilizer.

5. The water-absorbing resin as set forth in claim 4, wherein:

said dispersion stabilizer comprises at least one of a water-soluble polymer and a surface active agent.

6. The water-absorbent resin as set forth in claim 1, further comprising inorganic fine particles.

7. The water-absorbent resin as set forth in claim 6, wherein said inorganic fine particles are silica fine particles.

8. The water-absorbent resin as set forth in claim 6, wherein said inorganic fine particles are included in said water-absorbent resin in an amount of 0.01 wt %–5 wt %.

9. The water-absorbent resin as set forth in claim 1, having a cellular surface.

10. The water-absorbent resin as set forth in claim 1, wherein the expansion-diffusing pressure is not less than 40 kdyn/cm$^2$.

11. The water-absorbent resin as set forth in claim 1, wherein the water-absorbing rate is not more than 60 seconds.

12. The water-absorbent resin as set forth in claim 1, wherein the diffusion index is not less than 100 mm.

13. The water-absorbent resin as set forth in claim 1, having a particle diameter of 0.1 mm–1 mm.

14. The water-absorbent resin as set forth in claim 1, wherein a cross-linking density around a surface portion of the particle is higher than that in an inner portion of the particle.

15. The water-absorbent resin as set forth in claim 14, wherein:

said water-absorbent resin is a material of at least one kind selected from the group consisting of: a partially neutralized cross-linked polymer of polyacrylic acid, a cross-linked copolymer of isobutylene-maleic anhydride, a hydrolyzed crosslinked copolymer of acrylonitrile, a hydrolyzed crosslinked copolymer of acrylamide a cross-linked copolymer of acrylonitrile or copolymer of acrylamide, a cross-linked copolymer of acrylate-acrylamide, a cross-linked polymer of polyvinyl alcohol, a cross-linked polymer of modified polyethylene oxide, a cross-linked copolymer of acrylamide-2-methylpropanesulfonate, a cross-linked copolymer of (meth)acryloylethane sulfonate, cross-linked carboxymethylate cellulose and a cross-linked polymer of a cationic monomer.

16. The water-absorbent resin as set forth in claim 14, wherein:

said water-absorbent resin is a partially neutralized cross-linked polymer of polyacrylic acid.

17. The water-absorbent resin as set forth in claim 1, which is subject to surface processing using a cross-linking agent of 0.001–10 parts by weight with respect to 100 parts by weight of solid water-absorbent resin, the cross-linking agent exhibiting reactivity with a functional group of water-absorbent resin.

* * * * *